United States Patent [19]

Hatanaka et al.

[11] Patent Number: 4,488,810
[45] Date of Patent: Dec. 18, 1984

[54] CHEMICAL ANALYZER

[75] Inventors: Isamu Hatanaka, Kanagawa; Takashi Sekine; Kenichiro Yazawa, both of Saitama, all of Japan

[73] Assignee: Fuji Photo Film Co., Ltd., Kanagawa, Japan

[21] Appl. No.: 212,009

[22] Filed: Dec. 1, 1980

[30] Foreign Application Priority Data

Nov. 30, 1979 [JP] Japan ................. 54-154313

[51] Int. Cl.$^3$ ............................................. G01N 21/00
[52] U.S. Cl. ................... 356/244; 356/418; 356/445; 422/64
[58] Field of Search ............... 356/409, 414, 416, 418, 356/244, 38, 445, 448, 39; 422/64, 65, 66

[56] References Cited

U.S. PATENT DOCUMENTS

| 3,540,808 | 11/1970 | Harmon | 356/39 |
|---|---|---|---|
| 3,574,064 | 4/1971 | Binnings et al. | 250/461 B |
| 4,101,222 | 7/1978 | Mathisen | 356/244 |
| 4,116,564 | 9/1978 | Renaud et al. | 356/39 |
| 4,125,327 | 11/1978 | Margolis | 356/39 |
| 4,256,696 | 3/1981 | Soodak | 422/64 |
| 4,268,173 | 5/1981 | Barnard et al. | 356/445 |
| 4,279,514 | 7/1981 | Blumel et al. | 356/244 |

Primary Examiner—R. A. Rosenberger
Attorney, Agent, or Firm—Sughrue, Mion, Zinn, Macpeak, and Seas

[57] ABSTRACT

A chemical analyzer in which a component of a material to be analyzed acts on a coloring (dye forming) reagent in a reagent layer of the multi-layer type chemical analysis slide. The material to be analyzed is then maintained at a constant temperature for a predetermined period of time, after which the degree of coloration thereof is measured optically so that predetermined parameters of the material are measured with a very high accuracy. A conveying mechanism conveys the chemical analysis slides along an analysis path between two stationary temperature control plates. A first one of the plates having a cut therein has a heating element buried therein extending throughout the plate. The opposed plate has a heating element extending into regions not opposed by the cut in the first plate. The second plate has plural openings through which an irradiating light beam from a light source of a photometric mechanism and a reflection light beam from slides positioned over the openings pass. The lower plate has corresponding reference reflection plates at positions which are irradiated by the irradiating light beam.

7 Claims, 1 Drawing Figure

CHEMICAL ANALYZER

BACKGROUND OF THE INVENTION

In order to determine the concentrations of components such as glucose, and urea nitrogen in blood, heretofore a simple analysis method has been employed in which a coloration test sheet is used. More specifically, in the prior art method, the degree of coloration (i.e., dye formation) of a coloration test sheet is often visually compared with a sample of coloration of a component to be measured which was obtained using the same component a predetermined concentration and the concentration of the component is determined as a result of the comparison. However, that simple analysis method does not have a satisfactory accuracy because the degree of coloration of the coloration test sheet must be determined visually by the operator.

In order to overcome this difficulty, a variety of methods have been proposed in the art in which a reflection type densitometer is used to improve the accuracy of determination of desired parameters of components to be measured.

The dye formed in the coloration test sheet is unstable, because it changes with time, and sometimes fading occurs. Accordingly, for simultaneously processing a number of different samples of materials using coloration test sheets, errors unavoidably occur.

In order to eliminate this drawback, a method of automatically analyzing a component to be measured with an optical device and a device for practicing such a method have been proposed in the art. In accordance with this method and device, a predetermined amount of sample solution to be analyzed is placed on a multi-layer type chemical analysis slide, which was produced by shaping a multi-layer type chemical analysis material (film) into the form of a slide, and containing at least a spreading layer and a reagent layer. The multi-layer type chemical analysis slide is conveyed by a conveying device such as a conveying belt to a controlled-temperature heating unit where it is held at a constant temperature for a predetermined period of time. Thereafter, the slide is irradiated by a measuring irradiation light beam of a wavelength which has been preselected in accordance with the component to be measured and the reagent contained in the reagent layer to measure the reflection factor thereof from which the concentration of the component to be measured can be determined.

However, the automatic chemical analyzer as described above is disadvantageous in that it is considerably bulky because the heating unit must be provided separately from the conveying device making it impossible to miniaturize the analyzer. Moreover, the construction thereof is considerably intricate.

SUMMARY OF THE INVENTION

In view of the above-described difficulties accompanying a conventional chemical analysis method and device, an object of the invention is to provide a chemical analyzer which is simple in construction, small in size and high in analysis accuracy and efficiency.

Particularly, in accordance with the invention, there is provided a chemical analyzer in which a component in a material to be analyzed acts on a coloring (dye forming) reagent in the reagent layer of a multi-layer type chemical analysis slide and is then maintained at a constant temperature (incubated) for a predetermined period of time after which determination of the degree of coloration is performed optically thereby to effectively carry out the determination of the desired parameter of the material with high accuracy.

More speicifically, in accordance with the invention, a chemical analyzer includes a conveying mechanism for conveying along a chemical analysis path a chemical analysis slide including at least one layer into which a material including a component to be measured is impregnated, a driving mechanism for driving the conveying mechanism, temperature controlling means for maintaining the chemical analysis slide at a constant temperature, photometric means for measuring the reflection optical density of the chemical analysis slide, and means for determining a desired parameter of the material to be measured in accordance with the reflection optical density thus measured. The controlling means includes at least one stationary temperature control plate in one part of which a heater or a heating-/cooling element is provided. The conveying mechanism is slidably provided on the stationary temperature control plate. The temperature control plate has at least one opening through which an irradiating light beam from a light source in the photometric means and a reflection light beam from the chemical analyzing slide pass, and the temperature control plate has at least one reference reflection plate at a position which is irradiated by the irradiating light beam.

Preferably, the temperature controlling means includes first and second stationary temperature control plates with the first stationary temperature control plate having a temperature changing element, namely, heater or a heating/cooling element, in a region thereof which confronts the second stationary temperature control plates while the second stationary temperature control plate has a cut formed therein and a heater or a heating-/cooling element thereof extends over the entire area thereof. The conveying mechanism is preferably slidably provided between the first and second stationary temperature control plates.

The chemical analyzer may further include an optical position detecting mechanism for detecting the positions of the conveying mechanism. The first stationary temperature control plate may have an opening for discharging the chemical analysis slide.

In the chemical analyzer according to the invention, the means for maintaining the multi-layer type chemical analysis slide at a constant temperature is preferably a heating or heating and cooling electrical element such as a heater or a cooling element utilizing the Peltier effect.

DESCRIPTION OF THE PREFERRED EMBODIMENTS

Figure 1:
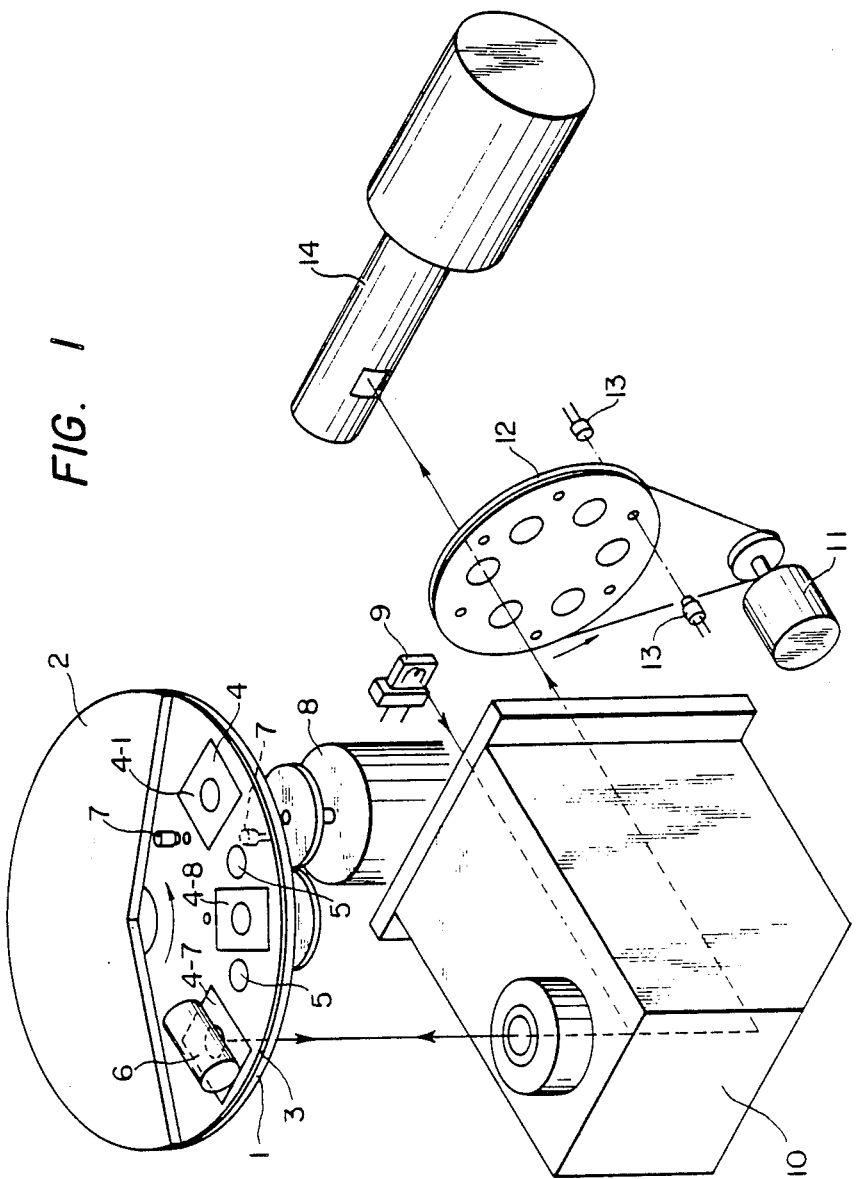
FIG. 1 is a schematic perspective view of a chemical analyzer according to the invention.

A preferred embodiment of a chemical analyzer according to the invention in which a heater is used to maintain the chemical analysis slide at a constant temperature will be described with reference to FIG. 1.

FIG. 1 is a schematic perspective view showing a preferred embodiment of chemical analyzer (colorimetric analyzer) constructed according to the invention. In FIG. 1, reference numerals 1 and 2 designate temperature control plates adapted to maintain a multi-layer type chemical analysis slide at a constant temperature.

Heaters are buried in the temperature control plates 1 and 2. However, it should be noted that, in order to correctly detect the start of heating, that is, the start of a constant temperature maintaining operation and to thereby make the constant-temperature maintaining period constant, the heater buried in the temperature control plate 2 extends throughout the entire area thereof while the heater buried in temperature control plate 1 does not extend into the region corresponding to a cut formed in the temperature control plate 2. The temperatures of the heaters are so controlled that a multi-layer chemical analysis slide undergoes a suitable coloring action.

A conveying member 3 is provided for conveying multi-layer type chemical analysis slides. More specifically, the conveying member 3 is rotatably supported between the temperature control plates 1 and 2 and is driven by a pulse motor 8 as shown in FIG. 1. The conveying member 3 has a plurality of multi-layer type chemical analysis slide holding sections 4 on its upper surface and at least one reference reflecting plate used as a reflection optical density comparison reference on its lower surface. In the case of FIG. 1, the conveying member 3 has eight multi-layer type chemical analysis slide holding sections 4-1 through 4-8.

Openings are formed in the temperature control plate 1 under the conveying member 3 through which reflection optical density measuring light emitted by a light source 9 is applied through a photometric head 10 to the multi-layer type chemical analysis slides. A guide roller 6 is provided for depressing the slides. A black material having a low reflection factor is disposed around the guide roller 6. Preferably, the outer wall of the guide roller is covered with lusterless black paint of lusterless black flocked fabric or black cloth having an optical density higher than 2.5. When a slide is placed on an opening in the temperature control plate 1, the guide roller 6 operates to bring the slide into close contact with the opening. When no slide is placed on the opening, the guide roller 6 operates to close the opening and hence, when no slide is placed on the opening, the reflection optical density of the guide roller 6 is measured. Accordingly, the absence of a chemical analysis slide to be measured can be detected when the reflection optical density of the guide roller 6 is measured. An optical detector 7 made up of a light emitting diode (LED) and a light receiving element, for instance, is provided for detecting the position of the conveying member 3.

Light which has been reflected by the slide is applied through the photometric head 10 and a filter disc 12 driven by a DC motor 11 to a photoelectric conversion and amplification device which is, for instance, a photomultiplier 14, with which a relative comparison is carried out using the level of light reflected by the reference reflection plate 5 as a reference signal to calculate the reflection optical density. According to the conparison result, the concentration of a material sample under measurement is colorimetrically determined and quantized. In a similar manner, other desired parameters or characteristics of the material under measurement can be determined. The filter disc 12 is provided which has a plurality of filters which are selectable according to the material to be measured. In order to select the proper filter, an optical detector 13 is provided similarly to the above-described optical detector 7.

A chemical analyzing procedure using the device shown in FIG. 1 will be described.

A material to be measured is disposed in the spreading layer of the multi-layer type chemical analysis slide. The material is spread uniformly into a spreading layer and is then allowed to permeate into the reagent layer below the spreading layer. The slide thus treated is manually or automatically inserted into the multi-layer type chemical analysis slide inserting section 4 through an inserting opening which is provided in a frame (not shown).

In the apparatus of FIG. 1, the slide is subjected to chemical analysis at the position indicated by 4-7. Upon completion of the insertion of the slide, the initial position of the conveying member 3 is detected by the optical detector 7 before the chemical analysis is started so that the slide conveyed to the position 4-7 by the conveying member 3 can be identified. Upon completion of the chemical analysis of the slide at the position 4-7, the slide is conveyed to the position 4-8 by the conveying member 3 which is driven by the pulse motor 8 so that it can be removed from the multi-layer type chemical analysis slide inserting section 4. In order to remove the slide, a simple arrangement may be employed in which an opening larger than the slide is formed in the region of the temperature control plate 1 which corresponds to the position 4-8 so that the slide can be released and allowed to fall by the force of gravity. A number of slides can be successively subjected to chemical analysis by inserting them one after another through the inserting opening into the slide inserting sections 4 which are afterwards emptied as described above.

In the case when the material to be measured and the reagent contained in the reagent layer are changed, the filter disc is turned by the DC motor 11 so that a filter suitable for use with the combination of material and reagent is disposed in the measurement optical path.

In the apparatus shown in FIG. 1, two temperature control plates 1 and 2 are provided. However, it should be noted that the invention is not limited thereto or thereby. The essential condition required for the temperature control plates is the provision of a temperature control plate in which the heater extends in the plate in the manner described above. The chemical analyzer according to the invention can operate satisfactorily without the temperature control plate 2. However, the use of two temperature control plates 1 and 2 is more effective with regard to thermal efficiency than the use of the only one temperature control plate. In the apparatus shown in FIG. 1, the filter disc 12 is disposed in the optical path of the reflection light. However, it may be provided in the optical path of the irradiating light between the light source 9 and the photometric head 10.

The chemical analyzer according to the invention may be employed for carrying out chemical analysis according to a so-called "velocity method" in which, in order to improve the chemical analyzing accuracy, two photometric systems are provided to measure two points on a multi-layer type chemical analysis slide the heating times of which are different in accordance with which measurement result the concentration can be determined. In this case, if a beam splitter or a mirror is disposed in the optical path between the slide and the photometric head 10 to deflect the optical path, measurement can be achieved with only a single photometric system.

As is clear from the above description, in the chemical analyzer of the invention, the conveying member 3 is slidably rotatable, at least on the temperature control plate which results in miniaturization of the analyzer.

Furthermore, in the chemical analyzer of the invention, the temperature is maintained constant by heating through contact and accordingly the chemical analyzer is more effective in thermal efficiency and higher in accuracy than a conventional device in which heating takes place through a layer of air. In addition, as the heaters are buried in particular designated regions of the temperature control plates according to the invention, the constant temperature maintaining period and the temperature itself can be readily and accurately controlled using a conventional simple temperature controller or by controlling the period of rotation of the pulse motor 8.

What is claimed is:

1. A chemical analyzer comprising: a conveying mechanism for conveying along a chemical analysis path a chemical analysis slide including at least one layer impregnated with a material including a component to be measured; driving means for driving said conveying mechanism; temperature controlling means for maintaining said chemical analysis slide at a constant temperature; means for measuring the reflection optical density of said chemical analysis slide; and means for determining the concentration of said predetermined component of said material to be measured in accordance with the reflection optical density thus measured, said constant temperature mechanism comprising at least one stationary temperature control plate in one part of which a temperature changing element is provided to thereby form a discrete heating area, said conveying mechanism being slidably provided on said stationary temperature control plate, said temperature control plate having (a) at least one opening outside the discrete heating area through which an irradiating light beam from a light source of said photometric mechanism and a reflection light beam from said chemical analysis slide pass, and (b) at least one reference reflection plate at a position which is irradiated by said irradiating light beam, said discrete heating area being formed such that said conveying mechanism has at least one chemical analysis slide holding section outside said discrete heating area for loading said chemical analysis slide, whereby an incubation time can be defined by both the rotation speed of the conveying mechanism and the form of the heating area such that chemical analyzer is capable of incubating said chemical analysis slide and measuring the reflection optical density of said incubated chemical analysis slide during one or less rotation of said conveying means.

2. The chemical analyzer as claimed in claim 1 wherein said constant temperature mechanism comprises first and second stationary temperature control plates, said first stationary temperature control plate having a temperature changing element in a region thereof which confronts said second stationary temperature control plate, said second stationary temperature control plate having a cut and having a temperature changing element in the entire area thereof, and said conveying mechanism being slidably provided between said first and second stationary temperature control plates.

3. The chemical analyzer as claimed in claim 1 or 2 further comprising optical position detecting means for detecting positions of said conveying mechanism.

4. The chemical analyzer as claimed in claim 1 or 2 wherein said first stationary temperature control plate is provided with an opening for discharging said chemical analysis slide.

5. The chemical analyzer as claimed in claim 1 or 2 further comprising a guide roller disposed for depressing slides and covering said at lest one opening when no slide is present.

6. The chemical analyzer as claimed in claim 1 or 2 further comprising a guide roller disposed for depressing slides and covering said at least one opening when no slide is present, the outer wall of said guide roller being covered with a material selected from the group consisting of lusterless black paint, lusterless black flocked fabric, and lusterless black flocked cloth having an optical density greater than 2.5.

7. The chemical analyzer as claimed in claim 1 or 2 further comprising a rotatable filter disc having a plurality of different filter elements disposed in openings therein, said filter disc being operatively disposed in one of the optical path of reflection light and the optical path of irradiating light.

* * * * *